(12) United States Patent
Saito et al.

(10) Patent No.: US 7,939,328 B1
(45) Date of Patent: May 10, 2011

(54) METHOD OF TRANSFORMING MONOCOTYLEDONS USING SCUTELLA OF IMMATURE EMBRYOS

(75) Inventors: Hideaki Saito, Iwata-gun (JP); Yuji Ishida, Iwata-gun (JP); Yukoh Hiei, Iwata-gun (JP); Toshihiko Komari, Iwata-gun (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 08/428,238

(22) PCT Filed: Sep. 1, 1994

(86) PCT No.: PCT/JP94/01442
§ 371 (c)(1),
(2), (4) Date: May 3, 1995

(87) PCT Pub. No.: WO95/06722
PCT Pub. Date: Mar. 9, 1995

(30) Foreign Application Priority Data

Sep. 3, 1993 (JP) .................................. 5-243975
Jan. 31, 1994 (JP) .................................. 6-027320

(51) Int. Cl.
*C12N 15/82* (2006.01)
(52) U.S. Cl. ........................... 435/469; 800/294
(58) Field of Classification Search ............... 435/172.3, 435/240.4, 240.48, 240.49, 240.5, 252.3, 435/172.1, 412, 424, 430.1, 430, 469; 47/58; 800/205, 300, 300.1, 320.1, 294, 295, 320, 800/320.2, 208; 536/23.1
See application file for complete search history.

(56) References Cited

U.S. PATENT DOCUMENTS

| 5,177,010 A |   | 1/1993 | Goldman ............... 435/172.3 |
| 5,350,688 A | * | 9/1994 | Matsuno et al. .......... 435/430.1 |
| 5,460,952 A |   | 10/1995 | Yu et al. |
| 5,591,616 A | * | 1/1997 | Hiei et al. .............. 435/172.3 |
| 5,712,112 A |   | 1/1998 | Yu et al. |

FOREIGN PATENT DOCUMENTS

| EP | 0604662 A1 | 7/1994 |
| JP | 7143895 A | 6/1995 |

OTHER PUBLICATIONS

Chan et al. "*Agrobacterium*-mediated production of transgenic reice plants expressing a chimeric alpha-amylase promtoer/beta-glucuronidase gene." Plant Molecular Biology vol. 22:pp. 491-506, 1993.*
Potrykus, Ingo "Gene Transfer to cereals; An Assessment." Biotechnology vol. 8 pp. 535-542, Jun. 1990.*
Bowen, B. Markers for plant gene transfer, vol. 1: 89-121, in Kung and Wu, eds, 1993, Transgenic Plants, vol. 1 and 2, SanDiego, Academic Press, see p. 90.*
Feldmann (1991, Plant Journal 1:71-82).*
Schläppi et al (1992, Plant Cell 4:7-16).*
Hiei et al, 1999, *Agrobacterium*-mediated transformation, In: Molecular Biology of Rice, Ko, ed, Springer-Verlag, Tokyo, p. 235-256.*
Hiei et al, 1997, Plant Mol. Biol. 35:205-218.*
Aldemita et al, 1996, Planta 199:612-617.*
Raineri et al (1990, Bio/Technol. 8:33-38).*
Chan et al (1993, Plant Mol. Biol. 22491-506).*
Ishida et al (1996, Nature Biotechnol. 14:745-750).*
Cheng et al, 1997, Plant Physiol. 115:971-980.*
Tingay et al, 1997, Plant J. 11:1369-1376.*
Hiei et al (1994, Plant J. 6:271-282).*
Usami et al 1987, Mol. Gen. Genet 209: 221-226.*
Chan et al Jun. 2003, Plant Molecular Biology 22: 491-506.*
Esau 1977, Anatomy of Seed Plants $2^{nd}$ Edition, John Wiley and Sons, New York, p. 477.*
Schlappi and Hohn (Jan. 1992, The Plant Cell 4: 7-16.*
Chang 1983 Plant Cell Reports 2: 183-185.*
Schläppi et al. (1992) *The Plant Cell* 4:7-16.
Sangwan et al. (1991) *Mol. Gen. Genet* 230:475-485.
Klein et al. (1988) *Bio/Technology* vol. 6, 559-563.
Mooney et al. (1991) *Plant Cell Tissue and Organ Culture* 25:209-218.
Raineri et. al. (1990) *Bio-Technology* 8:33-38.
Hiei et al. (1994) *The Plant Journal* 6(2): 271-282.
Christou et al. (1991) *Bio-Technology* 9:957-962.
Frame, Bronwyn R. et al., "Improved *Agrobacterium*-mediated transformation of three maize inbred lines using MS salts", Plant Cell Rep, 2006, vol. 25, pp. 1024-1034.
Mitic, N. et al., "*Agrobacterium*-mediated transformation and plant regeneration of *Triticum aestivum* L.", Biologia Plantarum, 2004, vol. 48, No. 2, pp. 179-184.
Hiei, Yukoh et al., "Improved protocols for transformation of indica rice mediated by *Agrobacterium tumefaciens*", Plant Cell, Tissue and Organ Culture, 2006, vol. 85, pp. 271-283.
Frame, Bronwyn R. et al., "*Agrobacterium tumefaciens*-mediated transformation of maize embryos using a standard binary vector system", Plant Physiology, May 2002, vol. 129, pp. 13-22.

* cited by examiner

*Primary Examiner* — David H Kruse
(74) *Attorney, Agent, or Firm* — Birch, Stewart, Kolasch & Birch, LLP

(57) ABSTRACT

Disclosed is a method of transforming monocotyledons which necessitates only a short period from the transformation to the regeneration of a whole plant as compared with the conventional methods, thus reducing the frequency of occurrence of mutants, and can be generally applied to the plants for which any system of regenerating the whole plants from protoplasts has not been established, and in which the material to be used can be readily prepared without any particular apparatuses. The present invention provides a method for transforming monocotyledons comprising transforming scutellum of an immature embryo of a monocotyledon with a bacterium belonging to genus *Agrobacterium* containing a desired gene, which immature embryo has not been subjected to a dedifferentiation treatment, to obtain a transformant.

24 Claims, 2 Drawing Sheets

METHOD OF TRANSFORMING MONOCOTYLEDONS USING SCUTELLA OF IMMATURE EMBRYOS

This application is the National phase application of PCT International Application No. PCT/JP1994/01442 filed on Sep. 1, 1994, which designated the United States. This application also claims priority under 35 U.S.C. §119(a) on Patent Application No(s). 243975/93 and 27320/94 filed in Japan on Sep. 3, 1993 and Jan. 31, 1994, respectively.

TECHNICAL FIELD

The present invention relates to a method for transforming monocotyledons.

BACKGROUND ART

Conventional methods for transforming monocotyledons include electroporation method, polyethylene glycol method (PEG method), particle gun method and so on.

The electroporation method is a method in which protoplasts and the desired DNA are mixed, and holes are formed in the cell membranes by electric pulse so as to introduce the DNA into the cells, thereby transforming the cells. Various genes have been introduced into monocotyledons, especially into rice plants by this method (Toriyama K. et al., 1988; Biotech. 6:1072-1074, Shimamoto K. et al., 1989; Nature 338:274-276, Rhodes C. A. et al., 1988; Science 240:204-207). However, this method has problems in that 1) it can be applied only to the plant species for which the system for regenerating plants from protoplasts has been established, 2) since it takes several months to regenerate plants from the protoplasts, a long period of time is required to obtain transformants, and 3) since the culture period is long, the frequency of emergence of mutants during the culture is high accordingly, so that the frequency of obtaining normal transformants is decreased.

The PEG method is a method in which the desired gene and protoplasts are mixed and the mixture is treated with PEG, thereby introducing the gene into the protoplasts. This method is different from the electroporation method in that PEG is used instead of the electric pulse. The efficiency of introducing the gene by this method is thought to be somewhat lower than that by the electroporation method. Although there are some reports mentioning that transformants were obtained by this method, this method is not widely used. As using protoplasts, this method has the same problems as in the electroporation method (Zhang W. et al., 1988; Theor. Appl. Genet. 76:835-840, Datta S. K. et al., 1990; Biotech. 8:736-740).

Recently, there has been a report of a method for introducing a gene into immature embryos weakly treated with a cell wall degrading enzyme and calli of maize by electric pulse (D'Halluin K. et al., 1992; Plant Cell 4:1495-1505). The existence of the introduced gene has been confirmed also in the regenerated plants. However, only one report that has disclosed the success in transformation has been made.

The particle gun method is a method in which the desired gene is attached to fine metal particles, and the metal particles are shot into cells or tissues at a high speed, thereby carrying out the transformation. Thus, according to this principle, transformation may be performed on any tissues. Therefore, it is said that this method is effective in transforming the plant species for which the systems for regenerating plants from protoplasts have not been established.

There have been made some reports of obtaining transformants of maize with normal fertility by transforming type II calli of maize (Armstrong C. L. and Green C. E., 1985; Planta 164:207-214) by the particle gun method (Gordon-Kamm W. J. et al., 1990; Plant Cell 2:603-618, Fromm M. E. et al., 1990; Biotech. 8:833-839, Walters D. A. et al., 1992; Plant Mol. Biol. 18:189-200, Vain P. et al., 1993; Plant Cell Rep. 12:84-88). However, almost all these reports used easily-culturable varieties as the starting materials and the techniques disclosed therein could not be applied to any unlimited varieties.

Vasil et al. obtained Basta-resistant calli and regenerated plants by introducing bar gene (Thompson C. J. et al., 1987; EMBO J. 6:2519-2523) capable of acetylating phosphinothricin, which is the main component in herbicides such as Basta, bialaphos, etc., and GUS gene into embryogenic calli of wheat by the use of a particle gun. They identified the activity of the enzyme which is a product from the introduced genes in these calli and regenerated plants and also identified the bar gene in them by Southern blot analysis (Vasil V. et al., 1992; Biotech. 10:667-674).

Li et al. obtained hygromycin-resistant, regenerated plants by introducing a hygromycin-resistant gene into immature embryos and embryogenic calli of rice by the use of a particle gun followed by selecting the transformants. They identified the hygromycin-resistant gene in the plants by Southern blot analysis. They revealed that the segregation ratio of the hygromycin-resistant and hygromycin-sensitive plants in the $R_1$ progeny of the plants was 3:1 (Li L. et al., 1993; Plant Cell Rep. 12:250-255).

Christou et al. obtained plants which are resistant to hygromycin or bialaphos and which have a GUS activity by introducing bar gene, a hygromycin-resistant gene and GUS gene into immature embryos of rice by the use of a particle gun, and they identified the introduced genes in the plants by Southern blot analysis (Christou P. et al., 1991; Biotech 9:957-962).

Koziel et al. obtained phosphinothricin-resistant plants by introducing bar gene and a Bt toxin-producing gene into immature embryos of maize by the use of a particle gun. They identified the production of a protein of Bt toxin in these plants and also the introduced genes therein by Southern blot analysis (Koziel M. G. et al., 1993; Biotech. 11:194-200).

Other methods include 1) culturing seeds or embryos with DNA (Topfer R. et al., 1989; Plant Cell 1:133-139; Ledoux L. et al., 1974; Nature 249:17-21), 2) treatment of pollen tubes (Luo and Wu, 1988; Plant Mol. Biol. Rep. 6:165-174), and 3) liposome method (Caboche M., 1990; Physiol. Plant. 79:173-176, Neuhaus G. et al., 1987; Theor. Appl. Genet. 75:30-36). However, these methods have problems in the efficiency of transformation, reproducibility or applicability, so that these methods are not popular.

On the other hand, a method for introducing a gene using the Ti plasmid of bacteria belonging to genus *Agrobacterium* as a vector is widely used for transforming dicotyledons such as tobacco, petunia, rape and the like. However, it is said that the hosts for the bacteria belonging to the genus *Agrobacterium* are restricted to only dicotyledons and that monocotyledons are not infected by *Agrobacterium* (De Cleene M., 1976; Bot. Rev. 42:389-466).

As for transformation of monocotyledons by *Agrobacterium*, although transformation of asparagus (Bytebier B. et al., 1987; Proc. Natl. Acad. Sci. USA, 84:5345-5349) and of *Dioscore bulbifera* (Schafer et al., 1987; Nature 327:529-532) have been reported, it is said that this method cannot be applied to other monocotyledons, especially to the plants belonging to the family Gramineae (Potrykus I., 1990; Biotechnology 8:535-543).

Grimsley et al. reported that T-DNA of *Agrobacterium* in which DNA of maize streak virus had been inserted was inoculated to the apical meristems of maize plants and infection of the plants by maize streak viruses was confirmed. Since the infected symptoms are not observed when merely the DNA of maize streak virus is inoculated thereto, they interpreted the above-mentioned result as a piece of evidence showing that *Agrobacterium* can introduce the DNA into maize (Grimsley et al., 1987; Nature 325:177-179). However, since it is possible that viruses replicate even if they are not incorporated into the nucleus genome, the result does not show that the T-DNA was incorporated into the nucleus. They subsequently reported that the infection efficiency is the highest when the *Agrobacterium* is inoculated to the apical meristems in the shoot apices of the maize (Grimsley et al., 1988; Biotech. 6:185-189), and that virC gene in the plasmid of *Agrobacterium* is indispensable to the infection (Grimsley et al., 1989; Mol. Gen. Genet. 217:309-316).

Gould et al. inoculated the apical meristems of maize with super-virulent *Agrobacterium* EHA1 having a kanamycin-resistant gene and GUS gene after having injured them with a needle, and selected the thus-treated apical meristems based on their resistance to kanamycin. As a result, plants having resistance to kanamycin were obtained. They confirmed by Southern blot analysis that some of the seeds of the subsequent generations of the thus-selected plants had the introduced genes (Gould J. et al., 1991; Plant Physiol. 95:426-434). This means that the plants grown from the *Agrobacterium*-treated apical meristems and selected on the basis of their resistance to kanamycin have both the transformed cells and non-transformed cells (chimera phenomenon).

Mooney et al. tried to introduce a kanamycin-resistant gene into embryos of wheat using *Agrobacterium*. The embryos were treated with an enzyme to injure their cell walls, and then cells of *Agrobacterium* were inoculated thereto. Among the treated calli, a very small amount of calli which are assumed to have resistance to kanamycin grew, but plants could not be regenerated from these calli. The existence of the kanamycin-resistant gene in them was checked by Southern blot analysis. As a result, in all of the resistant calli, the change in the structure of the introduced gene was observed (Mooney P. A. et al., 1991; Plant Cell, Tissue, Organ Culture, 25:209-218).

Raineri et al. inoculated 8 varieties of rice with super-virulent *Agrobacterium* A281 (pTiBo542) after having injured the scutella of the rice plants. As a result, the growth of tumor-like tissues was observed in two varieties, Nipponbare and Fujisaka 5. Further, cells of *Agrobacterium* containing a plasmid having a T-DNA from which a hormone-synthesizing gene had been removed and instead, a kanamycin-resistant gene and GUS gene had been inserted thereinto were inoculated to the embryos of rice. As a result, the growth of kanamycin-resistant calli was observed. Although the expression of the GUS gene was observed in these resistant calli, transformed plants could not be obtained from the calli. They interpreted from these results that the T-DNA of *Agrobacterium* was introduced into the rice cells (Raineri et al., 1990; Biotech. 8:33-38).

Thus, the experimental results which suggest that the introduction of genes into the plants belonging to the family Gramineae such as rice, maize and wheat can be attained by using *Agrobacterium* have been reported. However, all of these have a problem in the reproducibility and gave no convincing results since they did not fully identify the introduced genes (Potrykus I. 1990; Biotech. 8:535-543).

Chan et al. injured immature embryos of rice that had been cultured for 2 days in the presence of 2,4-D and then inoculated thereto cells of *Agrobacterium* having nptII gene and GUS gene in a medium containing potato suspension cultured cells. They cultured the thus-inoculated immature embryos on a G418-added medium to obtain regenerated plants from the induced calli. They investigated the existence of the GUS gene in the regenerated plants and these progeny by Southern blot analysis and found the existence of the introduced gene both in the $R_0$ and $R_1$ generations (Chan M. T. et al., 1993; Plant Mol. Biol., 22:491-506). These results support the transformation of rice with *Agrobacterium* but the frequency of transformation was as low as 1.6%. In addition, only one regenerated plant that had normally grown was obtained from the 250 immature embryos tested. The separation of immature embryos from rice plants needs much labor. Therefore, such a low transformation efficiency is not in a practical level.

DISCLOSURE OF THE INVENTION

As mentioned above, the introduction of genes into the plants belonging to the family Gramineae is now mainly carried out by the electroporation method and the particle gun method. In the electroporation method, however, since protoplasts are used, a long period of time and much labor are required to obtain regenerated plants. Further, there is a danger that mutants may emerge at a high frequency due to the long culturing period. Still further, this method cannot be applied to the plants such as maize for which the system for regenerating plants from protoplasts has not been established. A method has been reported in which genes are introduced into immature embryos that have been treated with an enzyme to such a degree that the cells therein are not made into protoplasts, by electric pulse (D'Halluin K. et al., 1992). However, only one success in the method is known so far. Therefore, it is difficult to say that the method is popular. Given the situations, the above-mentioned particle gun method has been applied to maize, using type II calli or immature embryos. The particle gun method give a high possibility of obtaining the intended transformants but needs a special apparatus, a particle gun. Without the apparatus, the particle gun method cannot be performed. In addition, the particle gun method has another problem in that fine metal particles scatter to often let the experimenters be in danger.

As for maize, a method for infecting its apical meristems with cells of *Agrobacterium* has been tried. (Gould J. et al., 1991). However, much labor is needed to isolate growth points from maize and it is not always easy to prepare a large amount of them. The present inventors tried to produce transformants of maize by this method but in vain (see Table 1 below).

Accordingly, the object of the present invention is to provide a method for transforming monocotyledons, with which the time required for obtaining regenerated plants from the time of transformation is shorter than that in the conventional methods, which can be generally applied even to the plants for which the systems for regenerating plants from protoplasts have not yet been established without requiring any special apparatuses, and with which the preparation of the materials to be used therein is easy.

The present inventors intensively studied the influences of the monocotyledonous plant tissues to be treated with *Agrobacterium*, the treatment conditions with *Agrobacterium*, the constitutions of the binary vectors, etc. on the introduction efficiency of genes into monocotyledons and, as a result, have discovered that immature embryos of monocotyledons to which a dedifferentiation treatment has not been performed can be transformed with bacteria belonging to genus *Agrobacterium* with drastically high efficiency, that the transforming method is reproducible, and that the above-mentioned object may be attained by this method, thereby completing the present invention.

Specifically, the present invention provides a method for transforming monocotyledons comprising transforming scutellum of an immature embryo of a monocotyledon with a bacterium belonging to genus *Agrobacterium* containing a desired gene, which immature embryo has not been subjected to a dedifferentiation treatment, to obtain a transformant.

The method of the present invention is the first that has made possible the reproducible introduction of a desired foreign gene into monocotyledons, for example plants of the family Gramineae such as rice, maize, wheat, barley, etc. Methods for transforming monocotyledons with cells of *Agrobacterium* have heretofore been known. As mentioned above, however, it is difficult to say that the known methods are established ones. According to the present invention, contrary to them, the immature embryos of monocotyledons, which have not been subjected to a dedifferentiation treatment, that have not been used in the prior art, are inoculated with cells of *Agrobacterium* by the improved method according to the present invention, thereby introducing a desired gene thereinto with ease. Since the method of the present invention employs immature embryos which may easily be prepared, the materials for the method may more easily be obtained than those for the prior art which employs the apical meristems of plants. In addition, since the transformation is effected on the scutella of immature embryos according to the method of the present invention, the time needed for regenerating plants from the resulting transformants may be shortened as compared with the transformation of protoplasts and, additionally, the frequency of mutation is lowered. When a super binary vector is employed in carrying out the present invention, it is possible to introduce a desired gene into varieties which are difficult to culture, such as maize or some varieties of rice, with high efficiency.

BEST MODE FOR CARRYING OUT THE INVENTION

Monocotyledons to be transformed by the method of the present invention are not restricted. The present invention may be applied to any monocotyledons such as, for example, rice, maize, wheat, barley, asparagus, etc. Preferred are plants belonging to the family Gramineae including rice, maize, barley, wheat, etc. Maize is best preferred.

The term "immature embryo" herein means the embryo of an immature seed which is in the stage of maturing after pollination. The maturing stage of the immature embryos to be treated by the method of the present invention are not restricted and the collected embryos may be in any stage after pollination. Preferred embryos are those collected on not less than 2 days after their fertilization. Also preferred are scutella of immature embryos capable of inducing dedifferentiated calli having an ability to regenerate normal plants after having been transformed by the method mentioned below. The immature embryos may preferably be inbreds, F1 between inbreds, F1 between an inbred and a naturally-pollinated variety, and commercial F1 varieties.

"Dedifferentiation treatment" means a process of obtaining cell clusters, such as callus, that show unorganized growth by culturing differentiated cells of plant tissues on a dedifferentiation medium.

As the *Agrobacterium* to be used for the transformation, *Agrobacterium* which have Ti plasmid or Ri plasmid and which have heretofore been employed for the transformation of dicotyledons can be employed. Many of these *Agrobacterium* contain a vector having a DNA region originated from the virulence region (vir region) of Ti plasmid originated from *Agrobacterium tumefaciens*. The gene encoding the character which is desired to be given to the plant is inserted in this vector, or exists in a separate plasmid and inserted into the Ti plasmid in vivo by homologous recombination or the like. Komari et al. developed a vector containing a DNA region originated from the virulence region (vir region) of Ti plasmid pTiBo542 contained in a highly virulent *Agrobacterium tumefaciens* A281 having an extremely high transformation efficiency (Hood, E. E. et al., 1984; Biotech. 2:702-709, Hood, E. E. et al., 1986; J. Bacteriol. 168:1283-1290, Komari, T. et al., 1986; J. Bacteriol. 166:88-94, Jin, S. et al., 1987; J. Bacteriol. 169:4417-4425, Komari, T., 1989; Plant Science, 60:223-229, ATCC 37349) (Japanese Laid-Open. Patent Application (Kokai) No. 4-222527). In this specification, this vector may be referred to as a "super binary vector". Such a super binary vector may be preferably employed in the present invention.

Figure 1:
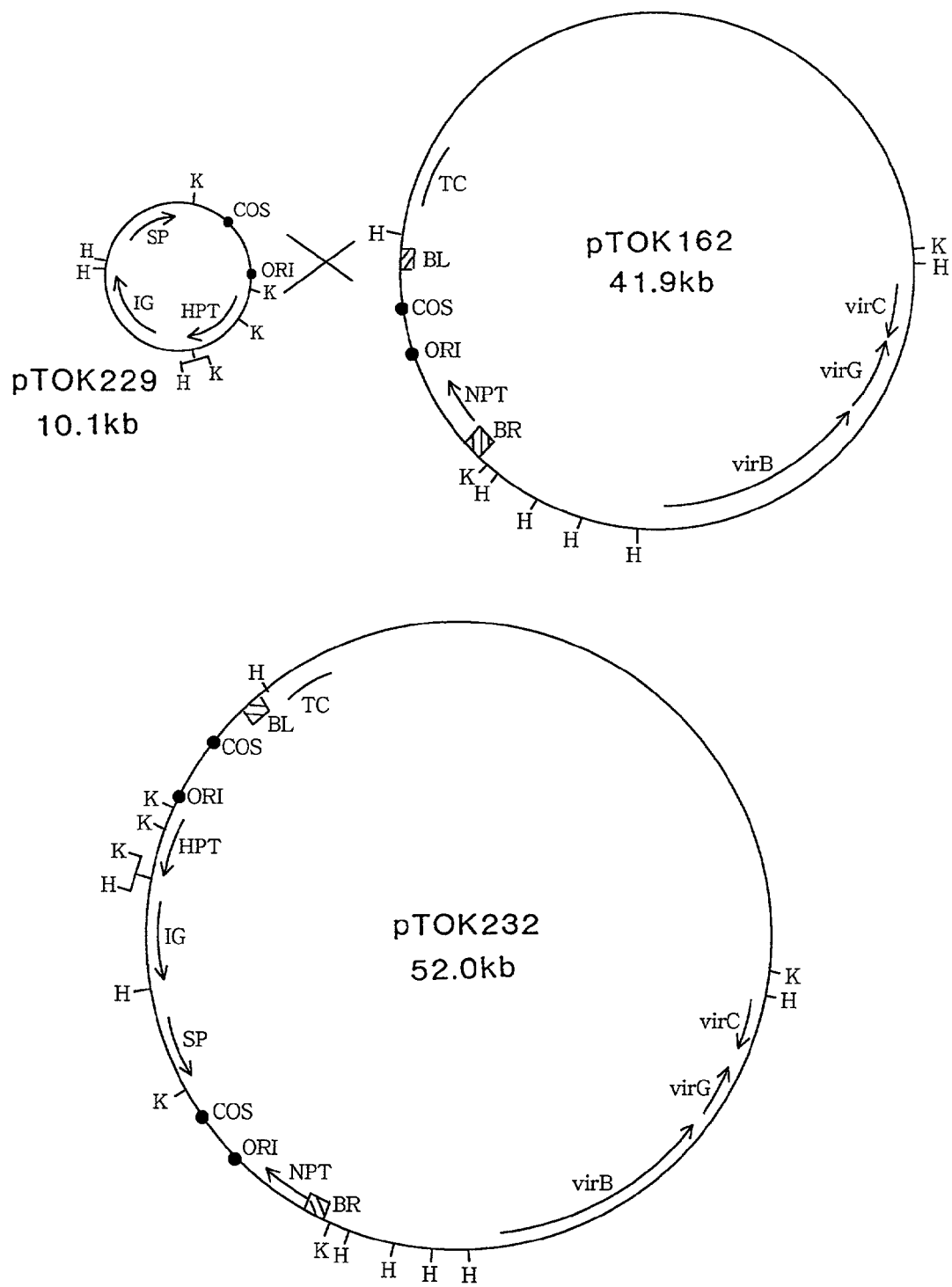
FIG. 1 shows the structure of pTOK162 which is one example of the plasmid contained in the bacteria of genus *Agrobacterium* usable in the present invention and the construction of plasmid pTOK232 used in the example of the present invention.

An example of such a super binary vector is pTOK162 (Japanese Laid-Open Patent Application (Kokai) No. 4-222527). Its structure is shown in FIG. 1. This plasmid comprises a plasmid called pTOK154 which can replicate in both *Escherichia coli* and in *Agrobacterium tumefaciens* (pTOK154 is a plasmid containing T region, which was constructed by the method described below from a known plasmid pGA472 derived from the Ti plasmid and a known plasmid having a wide host spectrum called pVCK101), into which a KpnI fragment (containing virB, virG and virC genes) with a size of 15.2 kb originated from the virulence region of pTiBo542 has been inserted, the KpnI fragment having been cloned. In pTOK154, between two border sequences of the T region, a kanamycin-resistant gene is inserted as a gene to be introduced into monocotyledons. This is an embodiment wherein the gene desired to be introduced into monocotyledons is arranged in a plasmid having the cloned DNA fragment originated from the virulence region of pTiBo542.

The gene which is desired to be incorporated into monocotyledons may be inserted into a restriction site in the T-DNA region of the above-described plasmid, and the desired recombinant plasmid may be selected depending on an appropriate selective marker such as drug resistance and the like which the plasmid has. However, if the vector, such as pTOK162 shown in FIG. 1, is large and has a number of restriction sites, it is not always easy to insert the desired DNA into the T region of the vector by conventional subcloning methods. In such a case, the desired DNA can be inserted into pTOK162 by utilizing the in vivo homologous recombination (Herrera-Esterella L. et al., 1983; EMBO J. 2:987-995, Horsch R. H. et al., 1984; Science 223:496-498) in the cells of *Agrobacterium tumefaciens*. That is, for example, pTOK162 is first introduced into *Agrobacterium tumefaciens* and the plasmid pBR322 (or a similar plasmid) containing the desired DNA is further introduced thereinto.

Since the DNA of pTOK162 has a region homologous with that of pBR322, the pBR322 derivative containing the desired gene is to be inserted into pTOK162 by the genetic recombination via the homologous regions. Unlike pTOK162, pBR322 cannot replicate by itself in *Agrobacterium tumefaciens*. Therefore, pBR322 can only be alive in *Agrobacterium tumefaciens* in the inserted form in pTOK162 (the recombined pTOK162 and pBR322 is hereinafter referred to as "pTOK162::pBR322 derivative"). By selecting the transformants based on the selective marker (such as drug resistance) specific to each of pTOK162 and pBR322 derivative, *Agrobacterium tumefaciens* transformants containing pTOK162::pBR322 derivative may be obtained. The present inventors made a study by introducing various plasmids into *Agrobacterium tumefaciens* containing pTOK162 to discover that, as the selection marker of the pBR322 derivative, spectinomycin-resistant gene (SP) originated from transposon Tn7 (De Greve, H. H. et al., 1981; Plasmid 6:235-248) is excellent. Thus, in cases where the desired gene has already been cloned into pBR322, by inserting SP gene into the plasmid, the desired gene can be inserted into the T region of pTOK162 by homologous recombination in vivo in *Agrobacterium tumefaciens*. Alternatively, a plasmid containing a DNA originated from pBR322 and SP gene is first provided, and the desired gene may be inserted into this plasmid. In this case, by utilizing the border sequences of the T region, it is possible to finally arrange the kanamycin-resistant gene and the desired gene in separate T regions in pTOK162. When plants are transformed using the resistance to kanamycin as a marker, there is a substantial probability that both T regions are introduced, and the introduction of the desired gene can be sufficiently attained. Further, in this case, since both T regions may be inserted into different chromosomes, it may be possible to subsequently segregate the desired gene from the kanamycin-resistant gene.

As the host bacteria belonging to genus *Agrobacterium*, *Agrobacterium tumefaciens* may preferably be employed, although not restricted.

The introduction of a plasmid into the bacteria belonging to the genus *Agrobacterium* such as *Agrobacterium tumefaciens* can be carried out by a conventional method such as triple cross method of bacteria (Ditta G. et al., 1980; Proc. Natl. Acad. Sci. USA, 77:7347-7351).

Since the *Agrobacterium* prepared as mentioned above has highly efficient virulence genes originated from pTOK162, transformation of monocotyledons can be attained with a high efficiency.

It should be noted that in the method of the present invention, the gene which is desired to be introduced into the monocotyledon is arranged between border sequences of the T region as in the prior art, and the desired gene may be arranged in the Ti plasmid or in another plasmid in the *Agrobacterium*.

The transformation of the immature embryos of monocotyledons by the *Agrobacterium* may be carried out by merely contacting the immature embryos with the *Agrobacterium*. For example, a cell suspension of the *Agrobacterium* having a population density of approximately from $10^6$ to $10^{11}$ cells/ml is prepared and the immature embryos are immersed in this suspension for about 3 to 10 minutes. The resulting immature embryos are then cultured on a solid medium for several days together with the *Agrobacterium*. The immature embryos to be transformed are directly subjected to transformation without being subjected to a dedifferentiation treatment such as by culturing them in the presence of 2,4-D. The conventional transformation of plants with the *Agrobacterium* is such that the immature embryos to be transformed therewith are dedifferentiated by culturing them in the presence of 2,4-D, before they are brought into contact with the *Agrobacterium*. The present inventors have found that the dedifferentiation is unnecessary according to the present invention. Therefore, the method of the present invention is superior to the conventional method in that the former is simpler than the latter. Some plants, especially maize often have a lowered transformation efficiency if subjected to the dedifferentiation treatment prior to the transformation. Therefore, the transformation efficiency of such plants may be elevated according to the method of the present invention in which the pre-treatment is not carried out. In addition, the conventional transformation of plants with the *Agrobacterium* employs a step of injuring plants or a step of treating them with an enzyme to digest the cell walls, thereby increasing the infection efficiency, prior to the their transformation with the *Agrobacterium*. The method of the present invention may have such pre-treatment, but the present inventors have found that efficient transformation may be attained by the method of the present invention even in the absence of such pre-treatment. In particular, injuring of maize plants results in the decrease in the rate for inducing calli after the transformation. For this reason, such pre-treatment is unfavorable for maize.

It is preferred that the thus-transformed immature embryos are thereafter dedifferentiated by a known method (Green, C. E. and Phillips, R. L., 1975; Crop Science 15:417-421, Duncan, D. R. et al., 1985; Planta 165:322-332) and the thus-dedifferentiated transformed cells are selected and grown. The selection may be effected on the basis of the expression of the above-mentioned desired gene. The dedifferentiated cells are desired to be in the form of calli having an ability to produce normal plants. The regeneration of plants from the transformed cells may be effected by known methods (Luppotto, E. and Lusardi, H. C., 1988; Maydica XXXIII:163-177). In this way, plants acquired the desired character by the transformation, preferably transformed plants acquired the desired character and having normal fertility can be regenerated. These steps are concretely illustrated in the following examples.

EXAMPLES

The present invention will be explained more concretely with reference to the following examples. It should be noted, however, that the present invention is not restricted to the examples.

(1) Preparation of Sample Tissues
(i) Varieties of Maize

Maize varieties of P3732, A188, H84, B37Ht, Mo17Ht, W117Ht, Oh43, H99, W64A Ht rhm, F1 (A188× Black Mexican Sweet), F1 (A188×B73Ht), F1 (B73Ht×A188), F1 (H84× A188), F1 (Mol7Ht×A188) and F1 (C103×A188) were selected as samples. The variety of P3732 was obtained from IWATA RAKUNOU KYODOKUMIAI. All the inbreds and the variety of Black Mexican Sweet were obtained from National Institute of Agrobiological Resources, Ministry of Agriculture, Forestry & Fisheries.

(ii) Variety of Rice

Rice variety of Tsukinohikari was selected as a sample.

(iii) Preparation of Shoot Apex Tissue of Maize

Seeds of Maize were immersed in 70% ethanol for one minute and then in 1% sodium hypochlorite for 5 minutes, and washed three times each with sterilized water. After the washing, these were placed on LS solid medium (LS major salts and LS minor salts (Linsmaier E. and Skoog F. 1965; Physiol. Plant. 18:100-127), 0.5 mg/ml of nicotinic acid, 0.5 mg/l of pyridoxine hydrochloride, 1 mg/l of thiamine hydrochloride, 100 mg/l of myo-inositol, 100 mg/l of casamino acid, 700 mg/12 of proline, 20 g/l of sucrose and 2.3 g/l of Gelrite) and cultured at 25° C. under illumination. After about 4 days, tissues with a length of about 0.1 mm×0.3 mm containing the apex dividing tissues were cut out from the grown young seedlings and used as samples.

(iv) Preparation of Immature Embryos of Maize

On about 14 days after pollination, immature embryos with a length of from 1 to 2 mm were aseptically isolated from female spikes.

(v) Preparation of Immature Embryos of Rice

The immature seeds were collected on 7 to 12 days after blooming and were sterilized by immersing them in 70% ethanol for 30 seconds and then in 1% sodium hypochlorite for 10 minutes after removing the glumes. The immature embryos were isolated from them and used as samples.

(2) Ti Plasmid

Hygromycin-resistant gene (HPT), phosphinothricin (PPT)-resistant gene (bar) and GUS gene were inserted into the T-DNA region of Ti plasmid to obtain the following plasmids:

(i) pIG121Hm:

A plasmid in which the GUS gene containing the first intron of the catalase gene of caster beans and a hygromycin-resistant gene were ligated (Nakamura et al., 1991; Plant Biotechnology II (Nakamura et al., Extra Issue of GENDAI KAGAKU, pp. 123-132), presented by Dr. Nakamura in Nagoya University).

(ii) pTOK232:

(a) Insertion of Intron GUS and Hygromycin-Resistant Genes into Intermediate Vector pTOK229

The ClaI fragment (2.5 kb) containing the spectinomycin-resistant gene originated from Tn7 was treated with Klenow fragment to blunt its ends. The resulting fragment was inserted into the SmaI site of pUC19 to obtain a plasmid pTOK107 (5.2 kb) having ampicillin-resistant and spectinomycin-resistant genes. The thus-obtained pTOK107 was treated with EcoRI and HindIII and the resulting 2.5 kb-fragment containing the spectinomycin-resistant gene was ligated to the EcoRI-HindIII fragment (2.7 kb) of pGA482 to obtain pTOK170 (5.2 kb) containing the spectinomycin-resistant gene and having HindIII and HpaI sites.

A vector pIG221 in which the first intron of the catalase of castor bean and GUS gene had been ligated to 35S promoter (Ohta et al., 1990, presented by Dr. Nakamura in Nagoya University) was digested with EcoRI and the resultant was treated with Klenow fragment to blunt its ends. Into the resultant, a HindIII linker (pCAAGCTTG; code 4660P commercially available from TAKARA SHUZO) was inserted. A fragment containing 35S promoter and intron GUS was cut out by digesting the resulting vector with HindIII, and the fragment was inserted into the HindIII site of a plasmid pGL2 (J. Paszkowski, obtained from Friedrich Miescher Institute) containing a hygromycin-resistant gene ligated to 35S promoter, to obtain pGL2-IG (7.6 kb). The above-mentioned plasmid pGL2 was obtained by inserting a hygromycin-resistant gene (Gritz L. and Davis J., 1983; Gene 25:179-188) into pDH51 (Pietrazak et al., 1986; Nucleic Acids Research 14: 5857-5868). The fragment obtained by treating pTOK170 with HpaI was ligated to a PvuII fragment (5.2 kb) of pGL2-IG to obtain pTOK229 (10.1 kb).

(b) Insertion into Super Binary Vector pTOK162

The insertion of the desired genes (hygromycin-resistant gene and intron GUS gene) into the super binary vector pTOK162 obtained by inserting virB, virC and virG genes originated from super-virulent Agrobacterium A281 into a super binary vector was carried out by homologous recombination. That is, since the both vectors contain a region originated from an E. coli plasmid pBR322, in the bacterial cells selected by resistances to spectinomycin and kanamycin, only the plasmid generated by recombination of the both plasmids is contained. The plasmid comprising the super binary vector in which the hygromycin-resistant gene and the intron GUS are inserted is referred to as pTOK232 (see FIG. 1).

Figure 2:
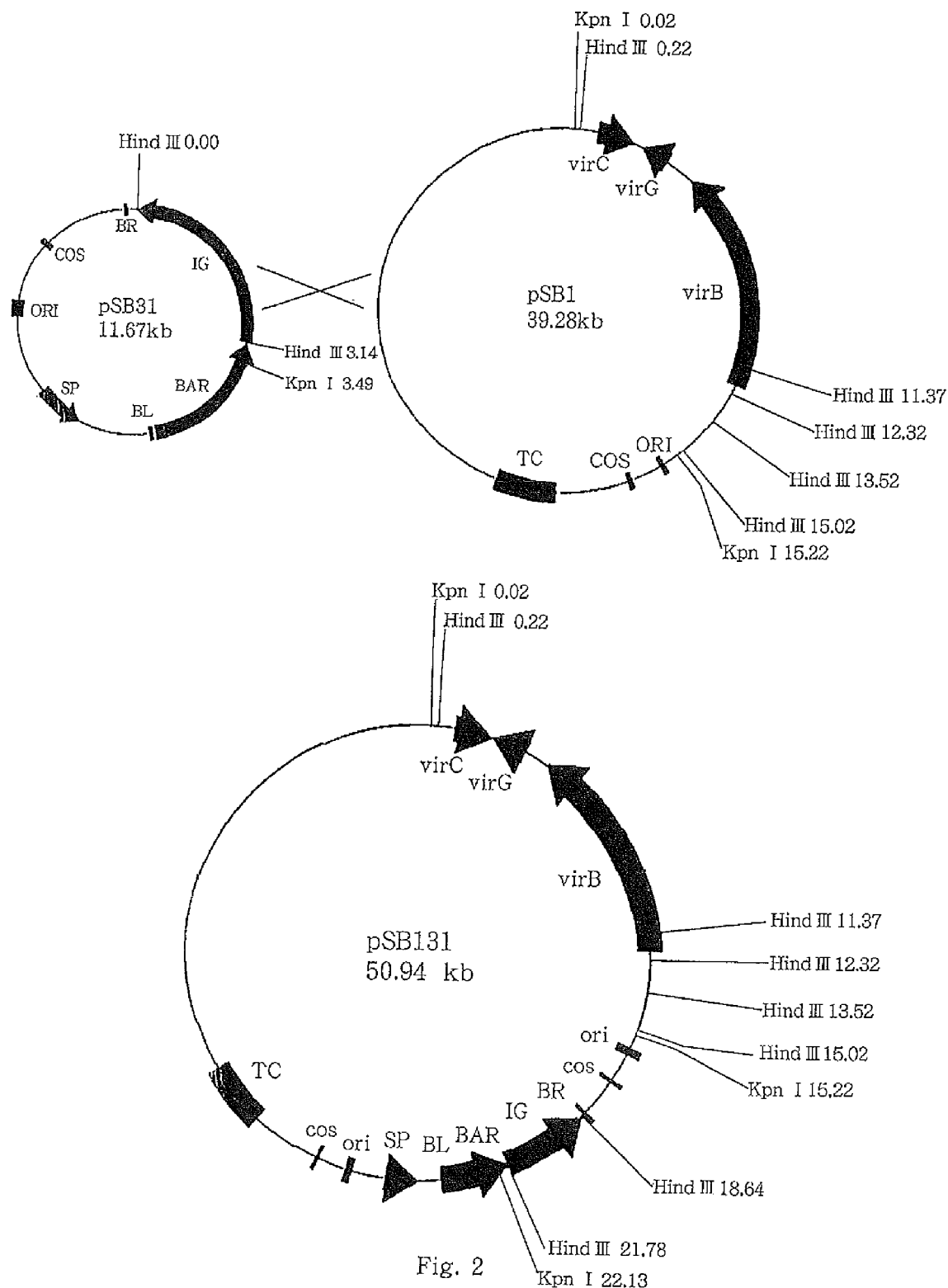
FIG. 2 shows the structure of pSB1 and the construction of plasmid pSB131, like FIG. 1.

In FIG. 1 and FIG. 2 mentioned below, "SP" means spectinomycin-resistant gene, "HPT" means hygromycin-resistant gene, "NPT" means kanamycin-resistant gene, "TC" means tetracycline-resistant gene, "BAR" means phosphinothricin-resistant gene, "IG" means intron GUS gene, "BR" means right border sequence of T-DNA, "BL" means left border sequence of T-DNA, "virB", "virB" and "virG" mean vir regions originated from super-virulent Agrobacterium A281, "ORI" means the replication origin of ColE1, "COS" means COS region of lambda-phage, "K" means restriction enzyme KpnI site, and "H" means restriction enzyme HindIII site.

(iii) pSB131:

(a) Construction of pSB131 pTOK170 was digested with BamHI and BglII and then circularized to give pYS138. This pYS138 was digested with EcoRI and Asp7181 and then treated with T4 DNA polymerase. Into this was inserted SalI liner (5'-GGTCGACC-3'), and the resultant was circularized to give pYS151. This pYS151 was digested with SalI, and a SalI fragment (4.7 kb) having T-DNA of pGA643 (An et al., Plant Molecular Biology Manual A3:1-19, Kluwer Academic, Dordrecht, 1988) was inserted into the cleaved site to give pTOK235. This pTOK235 was cleaved at its SacII site, its ends were blunted with T4 DNA polymerase, a HindIII linker (5'-CAAGCTTG-3') was inserted thereinto, and the resulting was circularized. The thus-obtained plasmid was referred to as pTOK246. This pTOK246 was digested with HindIII and EcoRI to remove most part of the T-DNA therein, and a HindIII-EcoRI fragment (2.2 kb) having a gene that had been prepared by ligating a phosphinothricin acetyl-transferase gene (Japanese Patent Kohyo Koho Hei-1-503434) to 35S promoter (bar gene having an ability to impart phosphinothricin resistant to plants) was inserted thereinto to obtain pSB25. Further, this pSB25 was digested with HindIII, and a HindIII fragment (3.1 kb) isolated from pIG221 and having 35S promoter and intron GUS was inserted thereinto to construct pSB31. That is, this pSB31 is an intermediate vector having the intron GUS gene and the phosphinothricin-resistant gene (bar) both expressing in plants.

(b) Construction of pNB1 pVCK101 (Knauf et al., Plasmid 8:45-54, 1982) was digested with EcoRI, treated with T4 DNA polymerase and circularized whereby its EcoRI site was deleted. This was further digested with BglII and then circularized whereby its BglII site was deleted. The resulting plasmid was named pVCK101Q. This pVCK101Q was digested with HindIII and XhoI and ligated to pUC18 that had been digested with HindIII and SalI, to give pTOK150. This pTOK150 was digested with HindIII and treated with T4 DNA polymerase. An EcoRI linker (5'-CCGAATTCGG-3') was inserted into the cleaved site and the resultant was then circularized to give pTOK239 having EcoRI site in place of HindIII site. pGA482 was digested with HpaI, an XhoI linker (5'-CCTCGAGG-3') linker was inserted thereinto, and the resultant was circularized to give pTOK236. This pTOK236 was digested with XbaI and EcoRI to isolate a 2.6 kb-fragment. pTOK239 was digested with EcoRI and XbaI to remove a 2.7 kb-fragment therefrom. The 2.7 kb XbaI-EcoRI fragment of pTOK236 was inserted into this and the resultant was circularized to give pNB1. This pNB1 is a kind of an acceptor vector and contains neither T-DNA nor virulence region-originated DNAs.

(c) Construction of pSB1 pNB1 was digested with KpnI, and a 15.2 kb-KpnI fragment having virB and virG genes in the virulence region of pTiBo542 (American Type Culture Collection accession No. 37349) was inserted thereinto. The resultant was circularized to give pSB1. This pSB1 is an acceptor vector. When an intermediate vector having T-DNA is inserted into this to give a hybrid vector, the resulting hybrid vector may be combined with a helper plasmid to construct a super binary vector.

(d) Insertion of pSB31 into pSB1

Like the case of pTOK232, pSB31 was inserted into pSB1 by homologous recombination to construct pSB131 (see FIG. 2).

(3) Host *Agrobacterium*

Strains LBA4404 and EHA101 from which T-DNA region was deleted were used as the host bacteria. Strain LBA4404 has a helper plasmid PAL4404 (having a complete vir region), and is available from American Type Culture Collection (ATCC 37349). Strain EHA101 has a helper plasmid having the vir region originated from a super-virulent *Agrobacterium* A281, and is available from Hood E. E. et al., 1986 (mentioned above).

The various binary vectors described in (2) were introduced into these two strains of *Agrobacterium*, and the strains described below were used for introducing the genes. The plasmids were introduced into the *Agrobacterium* strains by triple cross (Ditta G. et al., 1980; Proc. Natl. Acad. Sci. USA, 77:7347-7351).

LBA4404(pTOK232)
LBA4404(pSB131)
EHA101(pIG121Hm)

(4) Preparation of Suspension of Cells of *Agrobacterium*

Colonies obtained by culturing the *Agrobacterium* strains on AB medium (Drlica K. A. and Kado C. I., 1974; Proc. Natl. Acad. Sci. USA, 71:3677-3681) for 3 to 10 days were collected with a platinum loop and suspended in LS medium for cell suspension (comprising LS major salts, LS minor salts, 0.5 mg/ml of nicotinic acid, 0.5 mg/l of pyridoxine hydrochloride, 1 mg/l of thiamine hydrochloride, 100 mg/l of myo-inositol, 1.5 mg/l of 2,4-D, 1 g/l of casamino acid, 100 μM of acetosyringone, 0.2 M of sucrose and 0.2 M of glucose) for inoculation into maize plants but in modified AA medium (comprising AA major inorganic salts, AA amino acids and AA vitamins (Toriyama K. and Hinata K., 1985; Plant Sci., 41:179-183), MS minor salts (Murashige T. and Skoog F., 1962; Physiol. Plant., 15:473-497), 1.0 g/l of casamino acid, 100 μM of acetosyringone, 0.2 M of sucrose and 0.2 M of glucose) for inoculation into rice plants. The cell population of each medium was adjusted to be from $3 \times 10^9$ to $5 \times 10^9$ cells/ml. The suspensions were used for inoculation of plants.

(5) Conditions for Inoculation and Culture

The sample tissues were washed with sterilized water and immersed in the above-described suspensions of *Agrobacterium* strains for 3 to 10 minutes, after the shoot apex samples had been pierced with a glass needle (homemade) while the immature embryos were as they were. After the immersion, the shoot apex samples were transplanted on modified LS medium (comprising LS major salts, LS minor salts, 0.5 mg/ml of nicotinic acid, 0.5 mg/l of pyridoxine hydrochloride, 1 mg/l of thiamine hydrochloride, 100 mg/l of myo-inositol, 0.1 mg/l of kinetin, 1.0 mg/l of casamino acid and 2.3 g/l of Gelrite) containing 100 μM of acetosyringone, 20 g/l of sucrose and 10 g/l of glucose and cultured thereon at 25° C. under illumination for 2 to 3 days. Afterwards, these were washed with sterilized water containing 250 mg/l of cefotaxime and then continued to be cultured on the LS medium having the same concentration of cefotaxime. After the immersion, the immature embryos of maize were transplanted to LSD1.5 medium (comprising LS major salts, LS minor salts, 0.5 mg/ml of nicotinic acid, 0.5 mg/ml of pyridoxine hydrochloride, 1 mg/ml of thiamine hydrochloride, 100 mg/ml of myo-inositol, 1.5 ml/l of 2,4-D, 700 mg/l of proline, 500 mg/l of MES and 8 g/l of agar) containing 100 μM of acetosyringone, 20 g/l of sucrose and 10 g/l of glucose, and cultured at 25° C. in the dark for 1 to 5 days. Then, without being washed (this is because if washed, the regeneration rate of transformed plants becomes low), the thus-infected immature embryos were continued to be cultured on LSD1.5 callus-growing medium (having the same composition as the above-mentioned LSD1.5 medium, except that it does not contain glucose and acetosyringone) containing 250 mg/l of cefotaxime. On the other hand, the immersed immature embryos of rice were transplanted on 2N6 solid medium (comprising N6 inorganic salts and vitamins (Chu C. C., 1978; Proc. Symp. Plant Tissue Culture, Science Press Peking, pp. 43-50), 1 g/l of casamino acid, 2 mg/l of 2,4-D and 2 g/l of Gelrite) containing the same concentrations of acetosyringone, sucrose and glucose as mentioned above, and cultured at 25° C. in the dark for 2 to 5 days. Afterwards, the thus-infected immature embryos were washed with sterilized water containing 250 mg/l of cefotaxime and cultured on 2N6 solid medium having the same concentration of cefotaxime for 3 days to one week.

(6) Method for Examining GUS Activity

Immediately after the above-mentioned culture in the presence of *Agrobacterium* strains, the tissues were immersed in 0.1 M phosphate buffer (pH 6.8) containing 0.1% Triton X-100 at 37° C. for one hour. After washing off the *Agrobacterium* strains with the phosphate buffer, phosphate buffer containing 1.0 mM 5-bromo-4-chloro-3-indolyl-β-D-glucuronic acid (X-gluc) and 20% methanol was added to the tissues. After incubation at 37° C. for 24 hours, the number of blue-colored tissues were counted under a microscope and the percentages thereof based on the number of the samples tested are described. In the judgment of the GUS activities of the hygromycin-resistant calli and phosphinothricine-resistant calli which are thought to be transformed cells after selection, as well as in the judgement of the GUS activities of the transformed plants, parts of the resistant calli or plants were cut out from them and subjected to the same GUS staining.

(7) Selection of Transformed Cells and Regeneration of Plants

The *Agrobacterium*-infected immature embryos of maize were cultured on LSD1.5 callus-growing medium containing 250 mg/l of cefotaxime and from 0 to 100 mg/l of hygromycin or from 0 to 20 mg/l of PPT, for about 8 weeks to select resistant calli. These resistant calli were placed on LSZ medium (having the same composition as the LSD1.5 callus-growing medium, except that it does not contain 2,4-D but contains 50 mg/l of zeatin) and cultured at 25° C. under illumination, thereby regenerating the calli.

The immature embryos of rice were cultured on 2N6 solid medium containing 250 mg/l of cefotaxime and 50 mg/l of hygromycin for 3 to 4 weeks, and resistant calli were selected. Further, the resistant calli were cultured in N6-7 medium (comprising N6 inorganic salts, N6 vitamins, 2 g/l of casamino acid, 1 mg/l of 2,4-D, 0.5 mg/l of 6BA, 30 g/l of sorbitol, 20 g/l of sucrose and 2 g/l of Gelrite) containing 100 mg/l of hygromycin for 2 to 3 weeks, and then transplanted on N6S3 medium for regeneration of plants (comprising ½ concentrations of N6 major inorganic salts, N6 minor inorganic salts, N6 vitamins, 1 g/l of casamino acid, 0.2 mg/l of NAA, 1 mg/l of kinetin and 3 g/l of Gelrite) containing 50 mg/l of hygromycin. All the media used contained 250 mg/l of cefotaxime.

(8) Expression of Introduced Genes in Second-Generation of Maize Transformants

The first-generation transformed plants obtained by inoculation of LBA4404(pSB131) and selection by PPT were self-fertilized to obtain second-generation seeds. The seeds were sown and pieces of leaves were collected from young seedlings about 2 weeks after the sowing. The expression of the GUS gene was examined. In addition, to a part of the leaves of these young seedlings, 500-fold diluted Basta (a herbicide containing PPT as a major ingredient, commercially available from HOECHST) was applied and resistance to PPT was checked 2 weeks after the Basta-application. In addition, first-generation transformed plants were crossed with non-transformants (variety: A188) and immature embryos were collected about 2 weeks after the crossing, and the collected immature embryos were placed on LSD1.5 medium for callus induction containing 10 mg/l of PPT. The immature embryos were cultured at 25° C. for 3 weeks in the dark and the resistance to PPT was evaluated based on whether calli were formed or not by the culture. The transformed plants obtained by inoculation with LBA4404(pTOK233) and selection by hygromycin were also crossed with non-transformants (variety: A188) and the expression of GUS gene in young seedlings of the second-generation plants were examined.

(9) Analysis of Introduced Genes by Southern Blot Method

From the young seedlings of the first-generation transformants of maize that had been obtained by PPT selection after infected with the strain LBA4404(pSB131) and from the second-generation of plants, DNAs were extracted by the method of Komari et al. (Komari et al., 1989; Theor. Appl. Genet. 77:547-552). The thus-extracted DNAs were digested with a restriction enzyme BamHI. The resulting fragments were subjected to detection of the introduced genes by Southern blot analysis using the GUS gene and the bar gene as the probes. The length of the DNA region from the BamHI site in the T-DNA region to the terminal of the L border sequence was about 2.3 kb for the GUS gene and about 2.7 kb for the bar gene (see FIG. 2). The Southern blot analysis was carried out in accordance with the description in Molecular Cloning (Sambrook et al., 1989; Cold Spring Harbor Laboratory Press).

(10) Introduction of Gene into Shoot Apex Tissues of Maize

In order to confirm that the transformation employing the growth point tissues (shoot apex tissues) reported by Gould et al. (Gould J. et al., 1991; Plant Physiol. 95:426-434) can be attained, isolated shoot apex tissues of maize were treated with the above-described *Agrobacterium* strain EHA101 (pIG121Hm), and the GUS activity of the grown plants was determined. While expression of the GUS gene was not observed in the tissues not treated with the *Agrobacterium* strain, the expression of the GUS gene was observed in the spots pierced with the needle in the tissues treated with the *Agrobacterium* strain. The plants obtained by culturing the tissues were tested for their GUS activity. However, no plants exhibited the GUS activity. The vicinity of the growth point is a very fine tissue, so that it is not easy to pierce the needle into the very fine tissue to infect the tissue with *Agrobacterium*. The results of this experiment show that the transformation by infecting the vicinity of the growth point with *Agrobacterium* requires high skill in cutting out and piercing the growth point, etc.

TABLE 1

Introduction of Gene into *Maize* Shoot Apex Tissues

| Number of Sample Tissues | Number of Plants Grown | Number of Plants Obtained | Number of GUS+ Plants |
|---|---|---|---|
| 24 | 9 | 2 | 0 |
| 26 | 8 | 6 | 0 |
| 17 | 13 | 5 | 0 |
| 14 | 1 | 0 | 0 |
| 45 | 14 | 7 | 0 |
| 32 | 14 | 8 | 0 |
| 30 | 7 | 1 | 0 |

Sample variety was P3732 in all experiments.

(11) Inoculation into Immature Embryos of Maize

Immature embryos of various varieties of maize were treated with the *Agrobacterium* strain. The GUS gene was expressed at a high ratio in all the varieties of maize tested. The size of the GUS gene-expressed site in each sample tested was such that it was clearly observed visually. Thus, the GUS gene was expressed in wide range of cells. No difference was observed in the gene expression rate between the strains LBA4404(pTOK232) and LBA4404(pSB131). From the results, it is judged that immature embryos of maize are suitable as the materials to be infected and transformed with *Agrobacterium* at high efficiencies.

TABLE 2

Efficiency in Introduction of GUS Gene into *Maize* Immature Embryos

| Variety | Strain | Number of GUS+ Tissues/ Number of Sample Tissues |
|---|---|---|
| A188 | 1 | 32/32(100) |
| A188xB73Ht | 1 | 32/32(100) |
| B73HtxA188 | 1 | 76/77(99) |
| BMSxA188 | 1 | 63/63(100) |
| A188 | 2 | 65/66(98) |
| H84 | 2 | 26/30(84) |
| B37Ht | 2 | 20/20(100) |
| Mo17Ht | 2 | 24/25(96) |
| W117Ht | 2 | 15/15(100) |
| Oh43 | 2 | 17/20(85) |
| H99 | 2 | 25/25(100) |
| W64A Ht rhm | 2 | 10/10(100) |
| A188xB73Ht | 2 | 34/34(100) |
| B73HtxA188 | 2 | 49/49(100) |
| BMSxA188 | 2 | 59/59(100) |
| A188 | 3 | 15/16(94) |
| H84xA188 | 3 | 20/20(100) |
| Mo17Ht x A188 | 3 | 8/10(80) |
| C103xA188 | 3 | 11/11(100) |

BMS: Black Mexican Sweet
Strain 1: EHA101(pIG121Hm), 2: LBA4404(pTOK232), 3: LBA4404(pSB131)

(12) Inoculation into Pre-Cultured Immature Embryos of Maize (Comparative Example)

Chan et al. employed immature embryos of rice plants, that had been pre-cultured (dedifferentiation treatment) on $N_6RD$ medium (comprising $N_6$ inorganic salts, $N_6$ vitamins, 30 g/l sucrose, 2 mg/l 2,4-D, 8 g/l agarose) for 2 days, as the materials to be transformed with *Agrobacterium* (Chan M. T. et al., 1993; Plant Mol. Biol. 22:491-506). In order to reconfirm as to whether or not the Chan et al.'s method is effective also in the case employing immature embryos of maize plants, immature embryos of maize (variety: A188) that had been pre-cultured on LSD1.5 medium for callus induction for 2 days were tried to be transformed with *Agrobacterium*. The inoculation and the culture in the presence of *Agrobacterium* were carried out in the same manner as mentioned above. The *Agrobacterium* strain used was LAB4404(pSB131). As control, immature embryos of the same maize variety were subjected to the same test immediately after collected. On 3 days after the co-cultivation with *Agrobacterium*, the immature embryos of the both test groups were subjected to GUS staining. As a result, almost all the immature embryos tested immediately after collected were stained whereas none of the immature embryos tested after the pre-culture was stained (see Table 3). These results clearly indicate that transformation of maize is not attained if pre-cultured immature embryos of maize are employed.

TABLE 3

Introduction Efficiency of GUS Gene into Pre-cultured Immature Embryos of *Maize*

| Immature Embryos | Number of Sample Tissues | Number of GUS+ Tissues |
|---|---|---|
| Pre-cultured for Two Days | 21 | 0 |
| Immediately After Collection | 20 | 19 |

(13) Identification of Transformed Maize Cells

Calli that had been selected on a medium containing 30 mg/l or 50 mg/l of hygromycin and had been verified that they had hygromycin resistance on a medium containing 75 mg/l of hygromycin were subjected to GUS staining with the result that the all calli expressed GUS gene. The DNA that had been extracted from these calli according to the method of Komari et al. (Komari et al., 1989; Theor. Appl. Genet. 77:547-552) was used as a template to carry out polymerase chain reaction (PCR) using primers capable of amplifying the GUS gene (5'-ATGTTACGTCCTGTAGAAAC-3' (SEQ ID NO: 1), 5'-ATGGTGCGCCAGGAGAGTTG-3' (SEQ ID NO: 2)). The reaction was carried out, using 1 pi of the DNA solution, a mixture of the two primers of 5 pM each, 200 μM each of dATP, dCTP, dGTP and dTTP, a PCR buffer (commercially available from TAKARA SHUZO) and 2.5 U of Amplitaq DNA polymerase commercially available from TAKARA SHUZO), the total volume of the mixture being 100 μl. Thirty cycles of the reaction was repeated, according to the following temperature profile for one cycle: That is, the temperature profile for one cycle of the reaction comprised 94° C. for one minute, 55° C. for 2 minutes and then 72° C. for 3 minutes, all in a DNA THERMOCYCLER (commercially available from PERKIN ELMER CETUS CORP.) The PCR product was separated by electrophoresis on 0.7% agarose gel. When the DNA extracted from calli not infected with the *Agrobacterium* was used as the template, no amplified fragment of DNA was detected; whereas, when the DNA extracted from LBA4404(pTOK232) or the DNA extracted from the calli having the hygromycin resistance was used as the template, an amplified fragment of 1.8 kbp stained with ethidium bromide was detected by the electrophoresis. In addition, PCR was carried out employing primers capable of amplifying the 795 bp-region having the VirG initiation codon of the *Agrobacterium* (5'-GACGTTTATGAAGTAGGCGAGA-3' (SEQ ID NO: 3), 5'-TAAAAACGCGAGGAGAAGATTG-3' (SEQ ID NO: 4). When LBA4404(pTOK232) was used as the template, an amplified fragment of 0.8 kbp was detected; whereas, when the DNA extracted from the resistant calli and the DNA extracted from calli not infected with the *Agrobacterium* were used as the templates, no amplified fragment was detected. From these results, it was considered that the expression of the GUS gene in all the calli having the hygromycin resistance did not result from the *Agrobacterium* adhered to the calli but resulted from the introduced GUS gene and 20 that the compact and nodal calli that had grown in the media having stepwise-increased concentrations of hygromycin were transformants.

(14) Selection of Transformed Maize Plants

After co-cultivation with the *Agrobacterium*, hygromycin-resistant or PPT-resistant calli were selected on media containing from 30 to 100 mg/l of hygromycin or from 5 to 20 mg/l of PPT. In the former hygromycin selection, hygromycin-resistant calli were obtained from 11 to 27% of the immature embryos; while in the latter PPT selection, PPT-resistant calli were obtained from 35 to 64% of the Immature embryos (see Tables 4 and 6). These calli were placed on regeneration medium containing hygromycin or PPT, whereupon plants regenerated at a high frequency. The leaves of the regenerated plants were stained by GUS staining, resulting in expression of the GUS gene in many of the plants (see Tables 5 and 6). These data showed that these plants were transformed plants. The frequency of giving the transformed plants was especially high in the selection with PPT and there was little difference between the experiments, always giving independent transformed plants from 10% or more of the tested immature embryos (see Table 6). The results suggest that the method employed in these experiments is a stable transforming method capable of producing transformants at high frequency. Next, PPT-resistant calli that had been cultured and selected under the same conditions all the way from the inoculation to the propagation of calli were placed on a regeneration medium containing a high concentration (20 mg/l of PPT and a regeneration medium not containing PPT so as to check the GUS expression. In the plants regenerated on the medium containing PPT, the number of chimeric plants and escapes (GUS−) was small. This verifies the selection effect attained by the addition of PPT during the regeneration (see Table 7).

TABLE 4

Transformation Efficiency of *Maize* Immature Embryos by Hygromycin Selection

| Experiment | Process of Hygromycin Selection (mg/l) | Number of Hygromycin-resistant Calli/Number of Sample Immature Embryos (%) |
|---|---|---|
| 1 | 0-30-50 | 5/22(23) |
| 2 | 0-30-50 | 6/22(27) |
| 3 | 0-30-100 | 2/19(11) |

For the hygromycin selection, the calli were co-cultured with the *Agrobacterium* and then further cultured in the presence of hygromycin having the indicated concentrations each for 2 to 3 weeks.

TABLE 5

Selection Efficiency of Transformants in Hygromycin Selection

| Experiment | Number of Hygromycin resistant Calli | Number of Regenerated calli | Number of GUS+ Plants |
|---|---|---|---|
| 1 | 64 | 11 | 5 |
| 2 | 15 | 8 | 7 |
| 3 | 20 | 3 | 2 |

TABLE 6

Transformation Efficiency by PPT Selection

| Experiment | Number of Sample Immature Embryos | Number of Grown Immature Embryos | Number of Regenerated Immature Embryos | Number of GUS+ Plants (%) |
|---|---|---|---|---|
| 1 | 364 | 200(55) | 71(20) | 44(12) |
| 2 | 121 | 42(35) | 31(26) | 20(17) |
| 3 | 68 | 28(41) | 17(25) | 9(13) |
| 4 | 44 | 28(64) | 9(20) | 6(14) |

The number of the immature embryos and the number of the plants in this table are those not including clones.

TABLE 7

Influence of PPT Added to Regeneration Medium on Frequency of Regeneration and Transformation

| Added PPT | Number of Sample Calli | Number of Regenerated Calli | Frequency of GUS-stained Plants in Regenerated Plants | | |
|---|---|---|---|---|---|
| | | | GUS+ | Chimera | GUS− |
| + | 714 | 335(47) | 74 | 17 | 9 |
| − | 350 | 184(53) | 40 | 33 | 27 |

Concentration of Added PPT +: 20 mg/l, −: 0 mg/l

(15) Southern Blot Analysis of Introduced Genes in First-Generation Transformants of Maize Total DNA extracted from the transformant was digested with BamHI to obtain DNA fragments. These DNA fragments were subjected to Southern blot analysis, using bar gene or GUS gene as a probe, so as to detect the introduced gene in the first-generation transformants. As a result, the existence of the introduced gene was observed in all the tested transformants when either one of the genes was used as the probe. Number of copies of introduced genes were one or several. The BamHI fragment having bar gene in plasmid pSB131 had 2.7 kb and the BamHI fragment having GUS gene in plasmid pSB131 had 2.3 kb, while all the tested transformants each showed a band having about 3 kb or more. These results support introduction of bar gene and GUS gene into the plant chromosomes. Further, the lengths of the detected DNA fragments varied depending on their origins. This indicates that the genes were inserted in different regions in the maize chromosomes. Therefore, it was confirmed that the detected DNA fragments were not originated from the bacteria remained in the plants.

TABLE 8

Number of Copies of Introduced Genes in First-generation of Transformants Determined by Southern Blot Analysis

| Transformant (first-generation) | Number of Copies of Introduced Genes | |
|---|---|---|
| | bar | GUS |
| Control | — | — |
| Transformant 1 | 2 | 2 |
| 2a | 2 | 1 |
| 2b | 2 | 1 |
| 3 | 2 | 1 |
| 4a | 2 | 1 |
| 4b | 2 | 1 |
| 5 | 2 | 2 |
| 6 | 3 | 1 |
| 7 | 2 | 1 |

TABLE 8-continued

Number of Copies of Introduced Genes in First-generation of Transformants Determined by Southern Blot Analysis

| Transformant (first-generation) | Number of Copies of Introduced Genes | |
|---|---|---|
| | bar | GUS |
| 8 | 2 | 2 |
| 9a | 1 | 1 |
| 9b | 1 | 1 |
| 10 | 1 | 1 |

(16) Expression of Introduced Gene in Second-Generation of pTOK233-Introduced Maize Transformants Leaves of second-generation plants obtained by crossing the transformants obtained by hygromycin-selection with non-transformants were GUS-stained. The ratio of GUS-positive plants to GUS-negative plants was about 1:1 as expected (Table 9).

TABLE 9

Expression of Introduced Genes in Second-generation of Maize Transformants Obtained by Hygromycin-Selection

| Transformant | Number of Second-generation Plants Expression of GUS | |
|---|---|---|
| | Positive | Negative |
| Control | 0 | 5 |
| Transformant 11 | 4 | 5 |
| 12 | 5 | 6 |

(17) Expression of Introduced Genes in Second-Generation of pSB131-Introduced Maize Plants Leaves of non-transformed plants were GUS-stained and all of them were negative, while all of the leaves of the second-generation transformants obtained by self-fertilizing the transformants were GUS-positive except for one transformant. Further, Basta was applied to the leaves. As a result, all of the leaves of non-transformed plants died in about 2 weeks while the leaves of the transformants were healthy except for the GUS-negative plant (Table 10). Both the expression of GUS gene and the resistance to PPT exhibited genetic segregation in accordance with two-factor segregation. Furthermore, immature embryos collected from the non-transformed plants were cultured on a PPT-containing medium. As a result, the growth of the embryos was inhibited and no calli were induced. In contrast, with the immature embryos of both lines collected from the $R_0$ plants obtained by crossing the transformants and non-transformants, calli were induced from about 50% of the immature embryos placed and the calli well grew on the same medium (Table 11). The grown calli were GUS-stained. As a result, in all calli, the whole calli were stained in blue.

TABLE 10

Expression of Introduced Genes in Second-generation
of *Maize* Transformants Obtained
by PPT-Selection (Tested on Young Seedlings)

| Transformant | Number of Copies | | Number of Second-generation Plants | | | |
|---|---|---|---|---|---|---|
| | | | Resistance to PPT | | GUS | |
| | bar | GUS | Resistant | Sensitive | Positive | Negative |
| Control | — | — | 0 | 50 | 0 | 50 |
| Transformant 21 | 2 | 2 | 49 | 1 | 49 | 1 |

TABLE 11

Expression of Introduced Genes in Second-generation of *Maize*
Transformants Obtained by PPT-Selection
(Tested on Immature Embryos)

| Transformant | Number of Second-generation Immature Embryos Resistance to PPT | |
|---|---|---|
| | Resistant | Sensitive |
| Control | 0 | 76 |
| Transformant 31 | 29 | 32 |
| Transformant 32 | 22 | 25 |

(18) Southern Blot Analysis of Introduced Genes in Second Generation of pSB131-Introduced Maize DNAs were extracted from the second-generation plants obtained by self-fertilizing the transformant No. 21 shown in Table 10, and detection of the introduced genes were tried by the Southern blot analysis in the same manner as mentioned above. In all of the plants except for the plant which was GUS-negative and PPT sensitive, the introduced genes were detected when either of the genes was used as a probe (Table 12). The numbers of the copies of bar gene and GUS gene in the plants in which the existence of the introduced genes was confirmed were identical and the length of each band was identical to that detected in the first-generation plant. From these results, it was confirmed that the genes introduced into maize by utilizing *Agrobacterium* according to the method of the present invention are introduced into the nuclei of the plants and stably inherited to the next generation according to Mendel's laws.

TABLE 12

Number of Copies of Introduced Genes in Second-generation
of Transformants Determined by Southern Blot Analysis

| Transformant (second-generation) | Number of Copies of Introduced Genes | |
|---|---|---|
| | bar | GUS |
| Control | — | — |
| 21-1 | 1 | 1 |
| -2 | 2 | 2 |
| -3 | 1 | 1 |
| -4 | 1 | 1 |
| -5 | 0 | 0 |
| -6 | 1 | 1 |
| -7 | 1 | 1 |
| -8 | 2 | 2 |
| -9 | 1 | 1 |
| -10 | 2 | 2 |
| -11 | 1 | 1 |

(19) Inoculation of Rice Immature Embryos with *Agrobacterium*

High-rate expression of GUS gene was observed also in the rice immature embryos into which the GUS gene had been introduced, like in the maize immature embryos having the GUS gene. Especially, the expression of the GUS gene was observed at a high efficiency when the strain LBA4404 (pSB131) having the super binary vector was used (see Table 13).

TABLE 13

Efficiency of Introduction of GUS Gene into Rice
Immature Embryos

| Strain | Number of GUS+ Tissues/ Number of Treated Tissues (%) |
|---|---|
| Non-treatment | 0/50 (0) |
| EHA101(pIG121Hm) | 66/198 (33) |
| LBA4404(pTOK232) | 52/52 (100) |

The binary vectors used in this experiment did not cause expression of the GUS gene in the cells of the *Agrobacterium*. Based on the GUS gene in the rice immature embryos that had been co-cultured with the *Agrobacterium* as the index, it has been verified that the *Agrobacterium* cells are useful for inserting the gene into cells of maize and rice.

(20) Selection of Transformed Rice Plants

Rice immature embryos infected with the *Agrobacterium* were subjected to selection of hygromycin-resistant calli in a medium containing 50 mg/l of hygromycin. As a result, the resistant calli were obtained at a high rate when the strain having a super binary vector was used (see Table 14). The thus-selected calli produced regenerated plants with ease after transferred on a plant-regenerating medium containing the selection marker (see Table 14). The leaves of the regenerated plants were examined with respect to the GUS expression therein, with the result that the GUS gene was expressed in all the regenerated plants. These data showed that the regenerated plants were transformed plants. The *Agrobacterium* strain EHA101(pIG121Hm) has a virulence region of super-virulent pTiBo542 but does not have a super binary vector. The strains employed by Chan et al. were those of the same kind. Therefore, like the results of this example, they obtained extremely low transformation efficiency (Chan M. T. et al., 1993; Plant Mol. Biol., 22:491-506). The present example has clarified that the use of the strains having a super binary vector results in the production of the transformed plants from the rice immature embryos at drastically high efficiency.

TABLE 14

Results of Selection of Transformants on
Rice Immature Embryos

| Strain | Number of Tissues (%) | | | Drug Used for Selection |
|---|---|---|---|---|
| | Sample Immature Embryos | Resistant Calli | Calli from Which Plants were Regenerated | |
| non-treatment | 40 | 0 ( 0) | 0 ( 0) | HYG |
| EHA101(pIG121Hm) | 71 | 3 ( 4) | 1 ( 1) | HYG |
| LBA4404(pTOK232) | 77 | 23 (30) | 17 (22) | HYG |

HYG: hygromycin

(21) Identification of Gene Introduced into Rice Transformed Plants

To investigate the presence of the introduced gene, three random and independent transformed plants obtained by treating rice immature embryos with the strain LBA4404 (pTOK232) were subjected to polymerase chain reaction (PCR). The both ends of their structural regions were used as the primers for the GUS gene and the HPT gene. The DNA of the non-transformant and a plasmid DNA having each of GUS and HPT genes were used as a control. As a result, the three transformants obtained by the treatment with LBA4404 (pTOK232) gave an amplified fragment of 1.1 kb of the HPT gene, like those from the control plasmid. All the transformants having the GUS gene also gave an amplified fragment of 1.8 kb, like those from the control plasmid. However, non-transformants did not give these fragments. These results verified that all the sample plants tested in this experiment are transformed plants having the gene introduced by the *Agrobacterium*.

INDUSTRIAL AVAILABILITY

As mentioned above, the method of the present invention is a method for transforming monocotyledons, with which the time period required from transformation to regeneration of plants is short, which can be generally applied to the plants that have no method of regeneration of plants from protoplasts, which does not need a special equipment and in which the preparation of the material to be used is easy. Therefore, the present invention may be applied to breeding of monocotyledonous plants having desired characters.

The invention claimed is:

1. A method for transforming a monocotyledonous plant cell said method comprising contacting a cell of the scutellum of an immature embryo of the monocotyledonous plant with an *Agrobacterium* cell containing a T-DNA comprising a desired polynucleotide to be transformed into said cells of the monocotyledonous plant, to obtain a transformed scutellum cell, wherein the immature embryo has not been subjected to a preculturing step on a medium that induces callus.

2. The method according to claim 1, wherein said plant is maize.

3. The method according to claim 1, wherein said plant is rice.

4. A method for transforming a monocotyledonous plant cell said method comprising contacting a scutellum cell of an immature embryo of the monocotyledonous plant with an *Agrobacterium* cell containing a T-DNA comprising a desired polynucleotide to be transformed into said cell of the immature embryo of the monocotyledonous plant, wherein the immature embryo has not been subjected to a step of preculturing on a medium that induces callus, to obtain a transformed immature embryo cell, wherein said cell of the immature embryo is subjected to transformation without treatment of the immature embryo with an enzyme or without injury of the immature embryo prior to transformation.

5. The method according to claim 4, wherein said monocotyledonous plant is maize.

6. The method according to any one of claim 1 or 2-3, further comprising dedifferentiating the transformed scutellum cell and selecting and growing the transformed scutellum cell in a dedifferentiated state.

7. The method according to claim 6, further comprising regenerating a transformed, fertile plant from the transformed cell that has been selected and grown in a dedifferentiated state.

8. The method according to any one of claims 2 to 5, wherein said *Agrobacterium* cell contains a Ti plasmid or Ri plasmid and contains another plasmid comprising a DNA fragment comprising the virulence region of the Ti plasmid pTiBo542 of *Agrobacterium tumefaciens*.

9. The method according to claim 6, wherein said *Agrobacterium* cell contains a Ti plasmid or Ri plasmid and contains another plasmid comprising a DNA fragment originated from the virulence region of the Ti plasmid pTiBo542 of *Agrobacterium tumefaciens*.

10. The method according to claim 7, wherein said *Agrobacterium* cell contains a Ti plasmid or Ri plasmid and contains another plasmid containing a DNA fragment originated from the virulence region of the Ti plasmid pTiBo542 of *Agrobacterium tumefaciens*.

11. The method according to claim 1, wherein said *Agrobacterium* cell is *Agrobacterium tumefaciens*.

12. The method according to claim 1, wherein said *Agrobacterium* cell used for the contacting step of the transformation is a population of cells of $10^6$ to $10^{11}$ cells/ml.

13. The method according to claim 1, wherein said scutellum of immature embryo is obtained from an embryo that is not less than 2 days after pollination.

14. The method according to claim 1, wherein said immature embryo is obtained from a plant selected from the group consisting of a plant of an inbred line, a plant of an F1 hybrid between plants of inbred lines, a plant of an F1 hybrid between a plant of an inbred line and a naturally-pollinated variety of plant, or a commercial F1 hybrid varieties.

15. The method according to claim 6, wherein dedifferentiated transformed scutellum cells used for selection and growing are in the form of a callus.

16. A method for producing a transformed monocotyledonous plant said method comprising:
    transforming cells of the scutellum of an immature embryo of the monocotyledonous plant with an *Agrobacterium* cell containing a desired polynucleotide to be transformed into said cells of the monocotyledonous plant, to obtain transformed scutellum cells, wherein the immature embryo has not been subjected to a preculturing step on a medium that induces callus;
    culturing the transformed scutellum cells on a callus-inducing medium to obtain transformed callus tissue; and
    culturing the transformed callus tissue on a regeneration medium to obtain a transformed monocotyledonous plant.

17. The method according to claim 4, further comprising dedifferentiating the transformed immature embryo cell and selecting and growing the transformed immature embryo cell in a dedifferentiated state.

18. The method according to claim 17, further comprising regenerating a transformed, fertile plant from the transformed cell that has been selected and grown in a dedifferentiated state.

19. The method according to claim 18, wherein said *Agrobacterium* cell contains a Ti plasmid or Ri plasmid and contains another plasmid comprising a DNA fragment originated from the virulence region of the Ti plasmid pTiBo542 of *Agrobacterium tumefaciens*.

20. The method according to claim 4 or 5, further comprising dedifferentiating the transformed cell of the immature embryo and selecting and growing the transformed cell of the immature embryo in a dedifferentiated state.

21. The method according to any one of claims 2 to 5, wherein said *Agrobacterium* cell contains a Ti plasmid or Ri plasmid comprising the virulence region of the Ti plasmid pTiBo542 of *Agrobacterium tumefaciens*.

22. The method according to claim 6, wherein said *Agrobacterium* cell contains a Ti plasmid or Ri plasmid comprising the virulence region of the Ti plasmid pTiBo542 of *Agrobacterium tumefaciens*.

23. The method according to claim 7, wherein said *Agrobacterium* cell contains a Ti plasmid or Ri plasmid comprising the virulence region of the Ti plasmid pTiBo542 of *Agrobacterium tumefaciens*.

24. The method of claim 1, wherein the cell of the scutellum of the immature embryo is not treated with an enzyme and is not injured prior to transformation.

* * * * *

```
                             SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
atgttacgtc ctgtagaaac                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
atggtgcgcc aggagagttg                                                   20

<210> SEQ ID NO 3
<211> LENGTH: 22
<212> TYPE: DNA
<213> ORGANISM: Artificial Sequence
<220> FEATURE:
<223> OTHER INFORMATION: Synthetic primer

<400> SEQUENCE: 3
gacgtttatg aagtaggcga ga                                                22

<210> SEQ ID NO 4
<211> LENGTH: 22
<212> TYPE: DNA
<213> ORGANISM: Artificial Sequence
<220> FEATURE:
<223> OTHER INFORMATION: Synthetic primer

<400> SEQUENCE: 4
taaaaacgcg aggagaagat tg                                                22
```